United States Patent [19]

Calais et al.

[11] Patent Number: 5,731,462
[45] Date of Patent: Mar. 24, 1998

[54] PROCESS FOR OBTAINING N-MONOSUBSTITUTED HYDROXYLAMINE

[75] Inventors: Christophe Calais, Meyzieu; Rémy Teissier, Francheville, both of France

[73] Assignee: Elf Atochem S.A., Puteaux, France

[21] Appl. No.: 768,834

[22] Filed: Dec. 18, 1996

[30] Foreign Application Priority Data

Dec. 19, 1995 [FR] France .................. 95 15040

[51] Int. Cl.⁶ .................. C07C 249/02; C07C 249/00; C07C 209/40; C07C 209/00
[52] U.S. Cl. .................. 564/248; 564/268; 564/278; 564/301
[58] Field of Search .................. 564/248, 268, 564/278, 301

[56] References Cited

U.S. PATENT DOCUMENTS 3,337,631  8/1967  Gerjovich et al. .................. 564/248
4,898,901  2/1990  Ravichandran et al. .................. 564/248

FOREIGN PATENT DOCUMENTS 0 147 879 B1  12/1987  European Pat. Off. .
0 321 219 B1  2/1994  European Pat. Off. .

OTHER PUBLICATIONS

Hitoshi Mitsui et al., "Tungstate Catalysed Oxidation of Secondary Amines with Hydrogen Peroxide. A Novel Transformation of Secondary Amines into Nitrones," *J. Chem. Soc., Chem. Commun.*(1984), pp. 874–875.

Shun–Ichi Murahashi and Tatsuki Shiota, "Selenium Dioxide Catalyzed Oxidation of Secondary Amines With Hydrogen Peroxide. Simple Synthesis of Nitrones from Secondary Amines, " *Tetrahedron Letters*,vol. 28, No. 21 (1987), pp. 2383–2386.

Shun–Ichi Murahashi et al., "Tungstate–Catalyzed Oxidation of Secondary Amines to Nitrones. a–Substitution of Secondary Amines via Nitrones," *J. Org. Chem.*, vol. 55 (1990), pp. 1736–1744.

Shigeki Sakaue et al., "Oxidation of Aliphatic and Aromatic Amines with Hydrogen Peroxide Catalyzed by Peroxoheteropoly Oxometalates," *Chemistry Letters* (1992), pp. 289–292.

Enrico Marcantoni et al., "Oxidation of Secondary Amines to Nitrones Using Urea–Hydrogen Peroxide Complex (UHP) and Metal Catalysts," *Tetrahedron Letters*, vol. 36, No. 20 (1995), pp. 3561–3562.

*Primary Examiner*—Peter O'Sullivan
*Attorney, Agent, or Firm*—Pennie & Edmonds LLP

[57] ABSTRACT

The subject of the present invention is a new process for obtaining nitrones. It more particularly relates to a process for obtaining N-monosubstituted hydroxylamine comprising a stage in which a nitrone is formed from a secondary amine in the presence of an oxidizing agent and of at least one C=O containing species chosen from the group consisting of carbon dioxide, hydrogencarbonates and carbonates.

15 Claims, No Drawings

PROCESS FOR OBTAINING N-MONOSUBSTITUTED HYDROXYLAMINE

TECHNICAL FIELD

The subject of the present invention is a new process for obtaining nitrones. It more particularly relates to a process for obtaining N-monosubstituted hydroxylamine comprising a stage in which a nitrone is formed from a reaction of a secondary amine.

BACKGROUND OF THE INVENTION

Alkylhydroxylamines are known as free radical scavengers and reducing agents. They are used as polymerization inhibitors or corrosion inhibitors in the treatment of boiler water. In comparison with conventional corrosion inhibitors, such as hydrazine or sodium sulphite, alkylhydroxylamines exhibit the advantage of being able to protect not only the heating tube but also the condensation system. Thus, the whole of the plant for processing boiler water is protected against corrosion.

The synthesis of N-monosubstituted alkylhydroxylamines can be achieved according to various methods. A description is given in Patent EP 147,879 of a process for obtaining these alkylhydroxylamines by reduction of the nitroalkanes in the presence of a platinum-based hydrogenation catalyst and of additives, such as nitrogenous bases and organic trivalent or pentavalent phosphorus compounds. These alkylhydroxylamines are, however, unstable on storage (EP 321,219) and the process for obtaining them from the nitroalkanes exhibits the disadvantage of not being very selective.

Moreover, it is known that the acid hydrolysis of nitrones can result in N-monosubstituted alkylhydroxylamines.

Nitrones are important synthetic intermediates and excellent free radical scavengers. To date, all processes for obtaining nitrones from secondary amines involve catalysts based on transition metals. Thus, in J. Chem. Soc. Chem. Commun., p. 874 (1984), H. Mitsui et al. use 30% aqueous hydrogen peroxide solution and sodium tungstate in order to oxidize secondary amines to nitrones at 0° C. under argon. Dichloromethane is then employed as solvent in order to extract the nitrones from the reaction mixture.

Shun-Ichi Murahashi et al. (J. Org. Chem., 1990, 55, 1736–1744) have obtained a diisopropyl nitrone yield of 74% by oxidation of diisopropylamine with hydrogen peroxide in the presence of sodium tungstate. The solvent of the reaction is methanol.

According to the same author (Tetrahedron Letters, Vol. 28, No. 21, p. 2383–2386), nitrones can also be obtained by oxidation of secondary amines with hydrogen peroxide in the presence of selenium dioxide. Thus, the oxidation of diisopropylamine in methanol results in diisopropyl nitrone with a yield of 66%.

Heteropolyoxometallates, such as peroxotungstophosphates (PCWP), have also been employed for oxidizing secondary amines to nitrones. In this case, the temperature is 0° C. and the solvent is chloroform (S. Sakave et al. in Chemistry Letters, p. 289–292 (1992)).

According to E. Marcantoni et al. in Tetrahedron Letters, Vol. 36, No. 20, p. 3561–3562 (1995), secondary amines can be oxidized to nitrones with urea-$H_2O_2$ (UHP) complexes and in the presence of catalysts based on transition metals.

SUMMARY OF THE INVENTION

The subject of the present invention is a new process for obtaining nitrones. It more particularly relates to a process for obtaining N-monosubstituted hydroxylamine comprising a stage in which a nitrone is formed from a reaction of a secondary amine in the presence of an oxidizing agent and of at least one C=O containing species chosen from the group consisting of carbon dioxide, hydrogencarbonates and carbonates.

DETAILED DESCRIPTION OF THE INVENTION

A new process for obtaining nitrones in high yield has now been found which exhibits the advantage of being able to use water as solvent and which, moreover, does not involve catalysts based on transition metals. A process for obtaining N-monosubstituted hydroxylamine from a secondary amine and which does not exhibit the disadvantages set out above also forms the subject of the present invention.

The present invention also exhibits the advantage of resulting in a carbonyl coproduct (aldehyde or ketone) of economic value.

The aim of the present invention is therefore to provide a process for obtaining nitrone from a secondary amine comprising at least one hydrogen atom on at least one carbon atom alpha to the nitrogen, characterized in that this secondary amine is oxidized in the presence of an oxidizing agent and of at least one compound chosen from carbon dioxide, hydrogencarbonates and carbonates.

According to the invention, use may be made of a secondary amine of general formula:

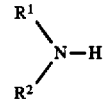

in which $R^1$ and $R^2$, which are identical or different, each represent a linear, branched or cyclic alkyl radical containing from 1 to 8 carbon atoms, such as, for example, methyl, ethyl, propyl, isopropyl, butyl, isobutyl, tert-butyl, amyl, hexyl or cyclohexyl radicals, an aryl radical, such as, for example, phenyl or tolyl radicals, or an aralkyl radical, such as, for example, the benzyl radical.

The $R^1$ and $R^2$ radicals can also be connected to one another, forming a substituted or unsubstituted ring, for example in pyrrolidine, piperidine, hexamethyleneimine or heptamethyleneimine.

Use is advantageously made of a non-cyclic secondary amine and preferably of a non-cyclic secondary amine in which the $R^1$ and $R^2$ radicals are identical.

Particularly preferred $R^1$ and $R^2$ radicals are those chosen from methyl, ethyl, propyl, isopropyl, butyl and isobutyl.

Use is preferably made of diisopropylamine.

The conversion of a cyclic or non-cyclic secondary amine to nitrone can be represented diagrammatically by the known equation below:

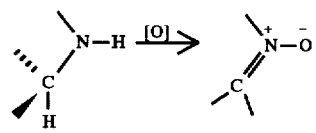

Although the formation of nitrone according to the present invention can be carried out in the absence of solvent, the reaction is preferably carried out in the presence of a solvent. The solvent can either be water or a polar organic solvent, such as methanol or acetone. The amount of solvent can vary within wide limits. Use is generally made of an amount such that the solvent/(secondary amine) ratio by mass is between 0.1 and 10 and preferably between 0.5 and 1. Use is advantageously made of water as solvent.

When the reaction is carried out in the presence of a solvent, the secondary amine can be introduced into the reactor before, during or after the introduction of solvent.

The temperature at which the secondary amine and optionally the solvent are introduced into the reactor is normally between room temperature and 70° C. It is preferable to introduce the secondary amine and, if appropriate, the solvent, at room temperature.

The oxidizing agent used in the process according to the present invention can be chosen from peroxides, hydroperoxides and peracids. Mention may be made, by way of example, of hydrogen peroxide, tert-butyl hydroperoxide or meta-chloroperbenzoic acid. Use is advantageously made of a hydrogen peroxide solution with an assay of between 5 and 70% by weight. Hydrogen peroxide concentrations of between 30 and 50% are particularly preferred.

The amount of oxidizing agent necessary for the conversion of a secondary amine to nitrone is generally in an (oxidizing agent)/(secondary amine) molar ratio of between 1 and 4, preferably in a molar ratio of approximately 2.

According to the present invention, the oxidizing agent is used in conjunction with at least one C=O containing species chosen from carbon dioxide, hydrogencarbonates and carbonates. This compound or these compounds is or are preferably introduced into the reaction mixture before the oxidizing agent.

Mention may be made, among hydrogencarbonates, of ammonium hydrogencarbonate or an alkali metal hydrogencarbonate, such as sodium hydrogencarbonate or potassium hydrogencarbonate.

Mention may be made, among carbonates, of ammonium carbonate or an alkali metal carbonate, such as sodium carbonate or potassium carbonate.

These C=O containing species are generally used in (C=O containing species)/(secondary amine) molar ratio of between 0.1 and 1 and most often of between 0.1 and 0.3.

Advantageously, carbon dioxide is used in conjunction with the oxidizing agent.

Use is generally made of a temperature of between 20° C. and 80° C. and preferably of between 50° C. and 70° C., for oxidizing the secondary amine to nitrone.

Although the oxidation of the secondary amine can be carried out at a pressure greater than atmospheric pressure, the reaction is most often carried out at atmospheric pressure.

The nitrone obtained in the process according to the invention can either be stored in solution or can be isolated from the reaction mixture by conventional methods (distillation, extraction) or can be hydrolysed directly to N-monosubstituted hydroxylamine.

The other subject of the invention thus relates to a process for obtaining N-monosubstituted hydroxylamine, according to which process the nitrone formed above is hydrolysed.

The process for obtaining N-monosubstituted hydroxylamine according to the invention is characterized in that the nitrone formed from a secondary amine, comprising at least one hydrogen atom on at least one carbon atom alpha to the nitrogen, using an oxidizing agent and in the presence of at least one compound chosen from carbon dioxide, hydrogencarbonates and carbonates, is hydrolysed.

The hydrolysis reaction of the nitrone can be carried out in the presence of an inorganic or organic acid. The inorganic acid is advantageously chosen from hydrochloric acid, sulfuric acid or phosphoric acid. Use is preferably made, as organic acid, of acetic acid or oxalic acid.

The acid is normally used in an (H$^+$)/(secondary amine) molar ratio of between 0.9 and 2 and preferably of approximately 1.

The hydrolysis temperature is preferably identical to that used in the stage of oxidation of the secondary amine, namely a temperature of between 20° C. and 80° C. and preferably of between 50° C. and 70° C.

The hydrolysis of the nitrone is generally carried out at a pressure below atmospheric pressure. Use may be made either of a constant reduced pressure or of a pressure which gradually decreases during the hydrolysis, so as to remove the carbonyl coproduct formed in the case of a non-cyclic nitrone.

The N-monosubstituted hydroxylamine formed can be isolated in the salt form by evaporation of the solvent under a reduced pressure.

The hydrolysis reaction of a non-cyclic nitrone can be represented diagrammatically according to the equation below:

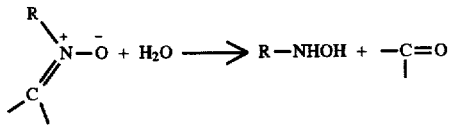

The particularly preferred N-monosubstituted hydroxylamine has the general formula: R—NHOH in which R is a methyl, ethyl, propyl, isopropyl, butyl or isobutyl radical. Advantageously, isopropylhydroxylamine is obtained in the process according to the present invention.

The water necessary for the formation of the N-monosubstituted hydroxylamine can be added before, during or after the introduction of the nitrone into the reactor or it can originate from the water used as solvent in the stage of formation of the nitrone.

Moreover, the hydrolysis of a cyclic nitrone results in a functionalized N-monosubstituted hydroxylamine comprising a carbonyl group.

Cyclic nitrone is understood to mean a nitrone in which the nitrogen atom forms part of a ring.

EXAMPLES

The invention will be better understood using the following examples:

General Procedure

The water, followed by the secondary amine to be oxidized, is introduced into a reactor thermostatically controlled at a temperature of between 17° and 30° C. Either the carbon dioxide and/or the hydrogencarbonate and/or the carbonate are then introduced into the reactor with stirring. After addition, the reaction mixture is brought to a temperature of between 50° and 70° C. over approximately 30 minutes. When the mixture has reached the predetermined temperature, the oxidizing agent is added over a period ranging from one hour to three hours.

The conversion of the secondary amine and the formation of the nitrone are monitored using gas phase chromatography (50 m Chrompack CPWAX 51 CB column, FID detector and analysis by temperature programming with internal standardization).

The nitrone formed can either be isolated from the reaction mixture after complete conversion of the secondary amine or can be directly hydrolysed. For the hydrolysis stage, the acid is introduced after complete consumption of the secondary amine and the pressure of the reaction mixture is then reduced to a value of between 300 and 500 mbar. After 2 to 4 hours, the pressure of the reaction mixture is again reduced to a value of between 20 and 150 mbar.

The N-monosubstituted hydroxylamine is then recovered in the salt form by evaporation under vacuum.

EXAMPLE 1

86 g of water and 170 g of diisopropylamine (DIPA, purity 99%) are introduced at room temperature into a thermostatically-controlled one-liter reactor. 17 g of $CO_2$ (Air Liquide N45, purity greater than 99.995%) are then introduced into the reactor. The mixture is then heated with stirring. When the temperature of the mixture has reached 65° C., the addition of a 45 wt. % aqueous hydrogen peroxide solution is begun. The addition of the 255 g of the aqueous hydrogen peroxide solution takes place over two and a half hours.

After complete consumption of the DIPA, i.e. approximately 4 hours (from the beginning of the reaction), the diisopropylnitrone is isolated.

The diisopropylnitrone yield is 95%.

EXAMPLE 2

This example is carried out in a way identical to Example 1, except that the diisopropylnitrone is not isolated but is directly hydrolysed.

Thus, after complete conversion of the diisopropylamine, 166 g of 37 wt. % hydrochloric acid are introduced. The pressure in the reactor is then reduced to 350 mbar in order to make possible the distillation of the acetone coproduced in the hydrolysis reaction. After three hours, the pressure is again reduced to 25 mbar. After complete removal of water, 170 g of crystalline N-isopropylhydroxylamine hydrochloride are recovered. This corresponds to a yield of 90% with respect to the starting amine.

EXAMPLE 3

The reaction is carried out under the same conditions as those described in Example 2, except that the following reactants are used:

| Diethylamine (DEA) | 125 g |
|---|---|
| Water | 120 g |
| $CO_2$ | 18 g |
| 45% $H_2O_2$ | 130 g |
| 37% HCl | 150 g |

Crystalline N-ethylhydroxylamine hydrochloride is obtained with a yield of 72%.

EXAMPLE 4

The operating conditions are the same as in Example 2, except that the reactor used has a capacity of 250 ml and that various acids were employed for the hydrolysis. The amounts of reactants are as follows:

| DIPA | 0.2 mol (20 g) |
|---|---|
| Water | 20 g |
| $CO_2$ | 2 g |
| 35% $H_2O_2$ | 20 g |
| Acid | 0.2 equivalent |

The corresponding crystalline salts of N-isopropylhydroxylamine (NIPHA) are obtained with the following yields:

| $(NIPHA)_2.H_2SO_4$ | 91% yield |
|---|---|
| $(NIPHA).CH_3COOH$ | 84% yield |
| $(NIPHA)_3.H_3PO_4$ | 87% yield |
| $(NIPHA)_2.H_2C_2O_4$ | 88% yield |

What is claimed is:

1. A process for obtaining nitrones from a reaction of a secondary amine, characterized in that this secondary amine, comprising at least one hydrogen atom on at least one carbon atom alpha to the nitrogen, is oxidized in a reaction mixture comprising an oxidizing agent and at least one added compound chosen from the group of C=O containing species consisting of carbon dioxide, hydrogencarbonates and carbonates provided that when carbon dioxide is the added compound, the concentration of carbon dioxide in the reaction mixture exceeds the naturally occurring concentration.

2. The process according to claim 1, characterized in that the oxidizing agent is hydrogen peroxide.

3. The process according to claim 1, characterized in that the reaction is carried out in the presence of a solvent.

4. The process according to claim 2, characterized in that the reaction is carried out in the presence of a solvent.

5. The process according to claim 3, characterized in that the solvent is water.

6. The process according to claim 4, characterized in that the solvent is water.

7. The process according to claim 1, characterized in that the secondary amine is diisopropylamine.

8. The process according to claim 1, characterized in that the temperature of the reaction mixture is between 20° C. and 80° C.

9. The process according to claim 8, characterized in that the temperature of the reaction mixture is between 50° C. and 70° C.

10. The process according to claim 1, characterized in that the (oxidizing agent)/(secondary amine) molar ratio is between 1 and 4.

11. The process according to claim 1, characterized in that the (C=O containing species)/(secondary amine) molar ratio is between 0.1 and 1.

12. The process according to claim 11, characterized in that the (C=O containing species)/(secondary amine) molar ratio is between 0.1 and 0.3.

13. The process for obtaining N-monosubstituted hydroxylamine, characterized in that the nitrone formed according to claim 1 is hydrolysed.

14. The process according to claim 13, characterized in that the hydrolysis of the nitrone is carried out in the presence of inorganic or organic acids.

15. The process according to claim 14, characterized in that the ($H^+$)/(secondary amine) molar ratio is between 0.9 and 2.

* * * * *